US00PP09944P

United States Patent [19]

Cornelis

[11] Patent Number: Plant 9,944

[45] Date of Patent: Jul. 1, 1997

[54] SPATHIPHYLLUM PLANT NAMED DOMINO

[75] Inventor: Daniel Cornelis, Merelbeke, Belgium

[73] Assignee: Milestone Agriculture, Inc., Apopka, Fla.

[21] Appl. No.: 629,008

[22] Filed: Apr. 8, 1996

[51] Int. Cl.[6] ..... A01H 5/00

[52] U.S. Cl. ..... Plt./88.1

[58] Field of Search ..... Plt./88.1

*Primary Examiner*—James R. Feyrer

*Attorney, Agent, or Firm*—C. A. Whealy

[57] ABSTRACT

A distinct cultivar of Spathiphyllum plant named Domino, characterized by its numerous leaves and side shoots giving a dense full appearance; compact plant habit; moderate growth rate; narrow, glossy, green and white variegated leaves that are held horizontal to the petiole; and numerous small white flowers.

2 Drawing Sheets

1

The present invention relates to a new and distinct cultivar of Spathiphyllum plant, botanically known as Spathiphyllum, and hereinafter referred to by the cultivar name Domino.

The new cultivar was discovered by the inventor in Merelbeke, Belgium, as a spontaneous mutation in a large population of plants of the cultivar Daniel (disclosed in U.S. Plant Pat. No. 8,655). The new cultivar was identified as a single plant within this population of plants of the cultivar Daniel that consistently had variegated leaves compared to plants of the cultivar Daniel that had non-variegated leaves.

Asexual propagation by division, of the new cultivar at Merelbeke, Belgium, has shown that the unique features of this new Spathiphyllum plant are stabilized and reproduced true to type in successive generations of asexual propagation.

The new Spathiphyllum has not been observed under all possible environmental conditions. The phenotype may vary somewhat with variations in environment such as temperature and light intensity, without, however, any variance in genotype. The following observations, measurements and comparisons describe plants grown in Kwintsheul, The Netherlands, in 12-cm containers in a glass greenhouse with an average day temperature of 22 C., an average night temperature of 20 C., and a light level of 200 to 225 lux.

The following traits have been repeatedly observed and are determined to be the unique characteristics of Domino. These characteristics in combination distinguish Domino as a new and distinct cultivar:

1. Numerous leaves and side shoots give a dense full appearance.
2. Compact plant habit.
3. Moderate growth rate.
4. Narrow, glossy, green and white variegated leaves that are held horizontal to the petiole.
5. Pure white spathe color.
6. Numerous small flowers per plant.

Compared to the mutation parent, the cultivar Daniel, the new Spathiphyllum has green and white variegated leaves and plants of the cultivar Daniel have non-variegated, solid green, leaves.

The accompanying colored photographs illustrate the overall appearance of the new cultivar, showing the colors as true as it is reasonably possible to obtain in colored reproductions of this type.

The first photograph comprises a top perspective view of a typical potted plant of Domino.

The second photograph comprises a top perspective view of typical leaves from a plant of Domino showing the various variegation patterns.

2

In the following description, color references are made to The Royal Horticultural Society Colour Chart except where general terms of ordinary dictionary significance are used.

Botanical classification: Spathiphyllum cultivar Domino.

Parentage: Spontaneous mutation of cultivar Daniel (U.S. Plant Pat. No. 8,655).

Propagation: By divisions or by tissue culture.

Plant description:

*Plant shape.*—Upright, inverted triangle, symmetrical.

*Growth habit.*—Erect when young, becoming outwardly spreading and arching as leaves develop. Numerous side shoots give plants a full, dense appearance. Compact plant habit, appropriate for 12-cm containers.

*Plant height.*—30 to 40 cm from soil level to top of leaf plane.

*Plant vigor.*—Moderate growth rate.

*Crop time.*—Sixteen weeks are usually require from planting of a young plant to a finished 12-cm container.

*Rooting habit.*—Freely branching, numerous fleshy roots with finer lateral roots.

*Foliage description.*—Leaf shape: Young: Narrowly elliptic. Mature: Narrowly elliptic. Leaf length: About 24 cm. Leaf width: About 7 cm. Margin: Entire. Leaf surface: Slightly wavy. Leaf tip: Acuminate. Leaf base: Obtuse. Leaf aspect: Mature leaves held close to perpendicular to petiole, 90° to 100° angle to petiole. Leaf texture: Leathery, smooth, glabrous. Leaf color: Young, top side: Glossy, mostly 137A with varying areas of 191A, 191B, 191C, 193A and 155C. Young, under side: Predominantly 137B with varying areas of 191A, 191B, 191C, 193A and 155C. Mature, top side: Glossy, prodominantly darker than 147A with varying areas of 191A, 191B, 191C, 193A and 155C. Mature, under side: Predominantly 137A with varying areas of 191A, 191B, 191C, 193A and 155C. Petiole length, primary shoot: 25 to 35 cm. Petiole diameter, primary shoot, just below geniculum: About 4 mm. Geniculum diameter, primary shoots: About 4.5 mm. Petiole wing, primary shoots: Apparent on lower 80% of mature leaf petiole. Petiole color: Young: 137C. Mature: Winged area: 137A. Above winged area: 137A. Geniculum: 137A. Venation: Top side: Sunken, color depends on variegation. Under side: Prominent, color depends on variegation.

Flower description:

*Flower arrangement.*—Slightly cupped spathe with spadix held 5 to 10 cm above the foliage. Numerous flowers arise from leaf axils.

*Spathe.*—Shape: Ovate. Size: Length: About 6 cm. Width: About 3 cm. Aspect: After unrolling, spathe is slightly cupped. Color: Before unrolling: Yellow white (8D). Open flower: White (155D) and shiny, spathe becomes green (144A) with age.

*Spadix.*—Size: Length: About 4 cm. Diameter: About 1 cm. Color: Initially yellow white (8D), becoming more yellow (8C) and eventually green with age.

*Peduncle.*—Aspect: Strong and erect. Size: Length: 35 to 50 cm. Diameter: About 4 mm.

Disease resistance: No known Spathiphyllum diseases observed to date on plants grown under commercial greenhouse conditions.

Seed development: Seed development has not been observed.

It is claimed:

1. A new and distinct cultivar of Spathiphyllum plant named Domino, as illustrated and described.

* * * * *

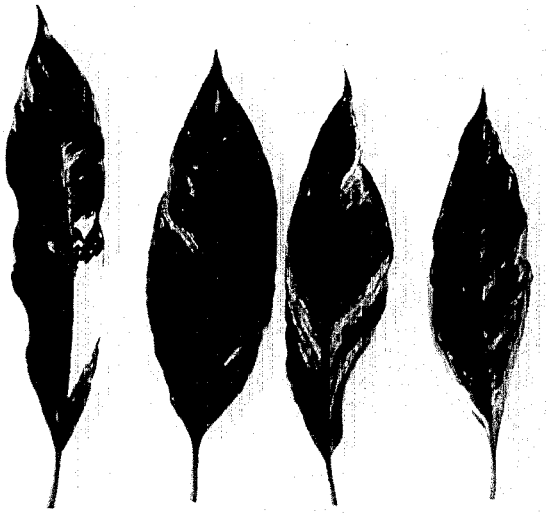

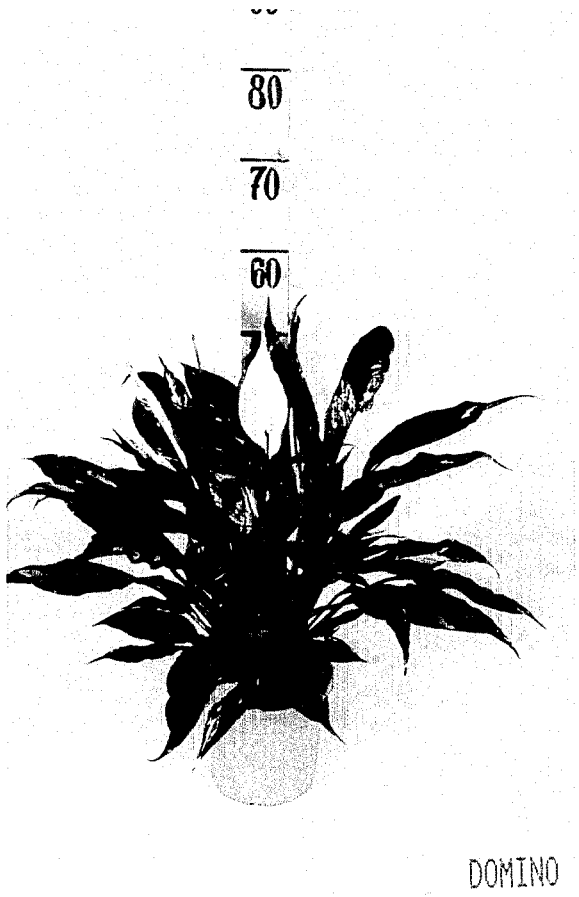
80
70
60
DOMINO